United States Patent [19]

Matsuo et al.

[11] Patent Number: 4,921,797
[45] Date of Patent: May 1, 1990

[54] C-TERMINAL ALPHA-AMIDATING ENZYME AND PROCESS FOR PRODUCTION AND USE THEREOF

[75] Inventors: Hisayuki Matsuo; Kensaku Mizuno, both of Miyazaki, Japan

[73] Assignee: Hisayuki Matsuo, Miyazaki, Japan

[21] Appl. No.: 58,919

[22] Filed: Jun. 5, 1987

[30] Foreign Application Priority Data

Jun. 7, 1986 [JP] Japan .............................. 61-131089

[51] Int. Cl.⁵ ...................... C12P 13/02; C12P 21/00; C12N 9/02; C12N 9/80
[52] U.S. Cl. .................................. 435/129; 435/189; 435/228; 435/68.1
[58] Field of Search ................... 435/228, 68, 70, 129, 435/189

[56] References Cited

U.S. PATENT DOCUMENTS 4,708,934 11/1987 Gilligan et al. .

FOREIGN PATENT DOCUMENTS

A8607607 12/1986 European Pat. Off. .

OTHER PUBLICATIONS

Murthy, A. S. N. et al. (1986), J. Biol. Chem. 261(4), 1815-1822.
Mollay, C. et al. (1986), FEBS Lett. 202(2), 251-254.
Mizuno, K. et al. (1986), Biochem. Biophys. Res. Commun. (1986), 137(3), 984-991.
A. F. Bradbury et al., Nature, vol. 298, pp. 686-688 (1982).
B. A. Eipper et al., PNAS, vol. 80, pp. 5144-5148 (1983).
I. Husain et al., FEBS Letters, vol. 152, pp. 277-281 (1983).
J. S. Kizer et al., PNAS, vol. 81, pp. 3228-3232 (1984).

Primary Examiner—Thomas G. Wiseman
Assistant Examiner—Charles L. Patterson, Jr.
Attorney, Agent, or Firm—Burns, Doane, Swecker & Mathis

[57] ABSTRACT

C-terminal α-amidating enzyme preparations, including preparations AE-I, AE-II, AE-IIa and AE-IIb, from the skin of *Xenopus laevis*, wherein all components can convert a peptide having a glycine residue at its C-terminal to a C-terminal amidated peptide lacking the glycine residue, and have a common N-terminal amino acid sequence represented by Ser-Leu-Ser---, and AE-I and AE-IIa have a molecular weight of about 39,000, AE-IIb has a molecular weight of about 34,000, and AE-II comprises two components having molecular weight of about 39,000 and 34,000; a process for production of the above-mentioned enzyme preparations; and a process for α-amidation of a peptide by using the above mentioned enzyme preparations.

12 Claims, 7 Drawing Sheets

C-TERMINAL ALPHA-AMIDATING ENZYME AND PROCESS FOR PRODUCTION AND USE THEREOF

BACKGROUND OF THE INVENTION

1. Field of the Invention

The present invention relates to a new C-terminal α-amidating enzyme preparation and a process for production and use thereof.

2. Description of the Related Art

A number of biologically active peptides isolated from neural or endocrine tissues have an α-amide structure at their carboxyl termini (C-termini). In most cases, the presence of the C-terminal α-amide structure is essential for their biological activity. Therefore, the C-terminal α-amide formation of the peptide is an important factor for in vivo activation of prohormones into active mature hormones. The recent elucidation of the nucleotides sequences of many precursors of α-amidated peptides shown that the amino acid residue that is α-amidated in the nature peptide is necessarily followed by a glycyl residue in the precursor. In procine pituitary, Bradburg, A. F. et al, Nature 298, 686–688, 1982, first characterized the α-amidating activity converting a synthetic substrate D-Tyr-Val-Gly to D-Tyr-Val-NH$_2$ and demonstrated that the C-terminal glycine in the substrate serves as a nitrogen-donor for α-amidation.

Because of the importance to clarify the mechanism of α-amide formation in tissues and of the promising usefulness of the enzyme for the production of C-terminally α-amidated peptides using, for example, recombinant DNA techniques, many attempts to purify the enzyme have been done but the engyme has not so far been obtained in a pure state. Eipper et al, *Proc. Natl. Acad. Sci. US*, 80, 5144–5148, 1983, reported that the α-amidating enzyme derived from pituitary gland requires copper cation and ascorbate for its activity. Husain, I. et al, *FEBS Lett.*, 152 227–281, 1983; and Kizer, J. S. et al, *Proc. Natl. Acad. Sci. US*, 81, 3228–3232, 1984, also reported a C-terminal α-amidating enzyme, but did not report a purified enzyme. Recently, Murthy A. S. N. et al, *J. Biol. Chem.*, 261, 1815–1822, partially purified a C-terminal amidating enzyme from pituitary gland of cattle, and showed that some types of enzymes having different molecular weights and electric charges are present. However, no type of enzyme has been homogeneously purified.

SUMMARY OF THE INVENTION

Accordingly, the present invention provides substantially purified C-terminal α-amidating enzyme products from the skin of *Xenopus laevis*, a process for production of the enzyme products, and a process for α-amidation of a peptide using the enzyme products. The enzyme products include AE-I, AE-II, AE-IIa, and AE-IIb.

More specifically, the present invention provides a substantially purified C-terminal α-amidating enzyme product AE-I from the skin of *Xenopus laevis*, characterized by the following properties:

(1) converting a peptide having a glycine residue at its C-terminal to a C-terminal amidated peptide lacking the glycine residue;

(2) having a molecular weight of about 39,000 as determined by SDS-polyacrylamide gel electrophoresis; and (3) having an N-terminal amino acid sequence represented by Ser-Leu-Ser - - - .

The present invention also provides a substantially purified C-terminal α-amidating enzyme product AE-II from the skin of *Xenopus laevis*, comprising two enzyme components wherein both components have a similar catalytic property and the same N-terminal amino acid sequence as the enzyme product AE-I, but one component has a molecular weight of about 39,000 and another component has a molecular weight of about 34,000.

The present invention also provides a substantially purified C-terminal α-amidating enzyme product AE-IIa obtainable by isolating one component from the above-mentioned enzyme product AE-II. The AE-IIa has a molecular weight of about 39,000, and a similar catalytic property and the same N-terminal amino acid sequence as the above-mentioned AE-I.

The present invention also provides a substantially purified C-terminal α-amidating enzyme product AE-IIb obtainable by isolating another component from the above-mentioned enzyme product AE-II. The AE-IIb has a molecular weight of about 34,000, and a similar catalytic property and the same N-terminal amino acid sequence as the above-mentioned AE-I.

Moreover, the present invention provides a process for the production of a substantially purified C-terminal α-amidating enzyme product from the skin of *Xenopus laevis*, comprising the following steps:

(a) preparing the skin of *Xenopus laevis*, (b) homogenizing the skin, (c) extracting the skin homogenate with a buffer to obtain a crude enzyme preparation, (d) fractionating the crude enzyme preparation into an enzyme fraction AE-I and an enzyme fraction AE-II by chromatography; and (e) optionally fractionating the enzyme fraction AE-II into an enzyme fraction AE-IIa and an enzyme fraction AE-IIb; and (f) purifying the fraction AE-I, AE-II, AE-IIa or AE-IIb to obtain an enzyme preparation AE-I having a molecular weight of about 39,000, AE-IIa having a molecular weight of about 39,000, AE-IIb having a molecular weight of about 34,000, or AE-II showing molecular weights of about 39,000 and 34,000, as determined by SDS gel electrophoresis.

Moreover, the present invention provides a process for C-terminal amidation of a peptide, characterized by incubating a starting peptide having glycine residue at its C-terminal with a C-terminal α-amidating enzyme preparation selected from the enzyme preparations defined in claims 1 to 3 or prepared by the process of claim 4 in an aqueous reaction medium to form a target C-terminal α-amidated peptide.

DESCRIPTION OF THE PREFERRED EMBODIMENT

Properties of the enzyme products

Figure 1:
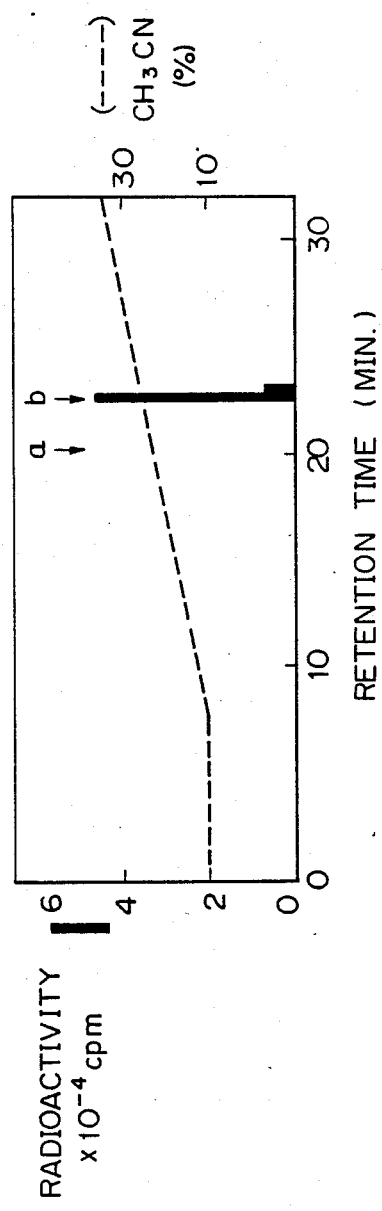
FIG. 1 represents an elution profile of a peptide amidated at its C-terminal with the present α-amidating enzyme product in reverse-phase high performance liquid chromatography (HPLC) using a ξBondapak C-18 column.

The C-terminal α-amidating enzyme AE-I of the present invention has the following properties:
(1) Action and specificity to substrates The enzyme converts a substrate peptide having a glycine residue at its C-terminal to a corresponding peptide α-amidated at its C-terminal and lacking the glycine residue. That is, the enzyme catalyzes the following reaction:

$$\text{peptide-Gly} \longrightarrow \text{peptide-NH}_2$$
$$\text{(I)} \qquad\qquad \text{(II)}$$

In the substrate (I) a glycime residue at its C-terminal is essential, and this glycine is a donor of nitrogen in the C-terminal amide group of the product shown by (II).
(2) The enzyme has a molecular weight of about 39,000 as determined by SDS-polyacrylamide gel electrophoresis.
(3) Optimum pH The optimum pH is 6 to 7.
(4) Effect of substances on enzyme activity (a) The $Cu^{++}$ cation is essential for enzyme activity. Although the enzyme is inhibited by 0.1 mM EDTA, the presence of an additional more than 0.12 mM $CuSO_4$ restores the enzyme activity.

(b) The enzyme is inhibited by 1 mM dithiothreitol. The presence of an additional 1.2 mM $CuSO_4$ or 5 mM N-ethylmaleimide restores the enzyme activity inhibited by the thiol compound.

(c) The enzyme exhibits lower enzyme activity unless ascorbate is present in a reaction mixture.
(5) Amino acid sequence The enzyme has an amino acid sequence Ser-Leu-Ser - - - at its N-terminal.

The enzyme product AE-II comprises two enzyme components, i.e., an enzyme component AE-IIa having a molecular weight of about 39,000 and enzyme component AE-IIb having a molecular weight of about 34,000.

The enzyme product AE-II is separated from the enzyme product AE-I in the step of hydroxylapatite column chromatography, as described below, and has a similar catalytic property.

The enzyme products AE-IIa and AE-IIb can be obtained by separating the above-mentioned components of the product AII by reverse-phase HPLC.

Process for production of the enzyme products

C-terminal α-amidating enzymes of the present invention can be extracted from the skin of *Xenopus laevis*. For the extraction, the skin is removed from *Xenopus laevis*, and the removed skin is homogenized with an appropriate buffer at a pH of 6 to 8, to dissolve the target enzymes. The solution containing the enzymes is then treated according to a conventional procedure to recover and purify the target enzymes. For example, the enzyme solution thus obtained is centrifuged to eliminate insoluble materials, and to a supernatant, ammonium sulfate is added to 80% saturation for salting out the enzymes. The whole is then centrifugated to recover a precipitate. The precipitate is dissolved in an appropriate medium, and the solution is dialyzed. The dialyzed solution is applied to a DEAE cellulose DE-52 column and eluted with a linear gradient of sodium phosphate buffer. Next, eluted fractions containing enzyme activity are subjected to affinity chromatography using an Affi-Gel Blue column which is eluted by an NaCl linear gradient elution. The eluted active fractions are then filtered through a Sephacryl S-300 column, and purified by a hydroxylapatite column to obtain two active fractions AE-I and AE-II. Among the active fractions, a major active fraction (fraction I in FIG. 3) is further purified by a hydroxylapatite column, and the purified active fraction is subjected to gel-filtration using Superose 12 to obtain a finally purified product of the C-terminal α-amidating enzyme AE-I of the present invention.

On the other hand, a minor active fraction (fraction II in FIG. 3) from the above-mentioned hydroxylapatite column is purified according to the same procedure as described for the major active fraction, to obtain a preparation of enzyme AE-II. The enzyme preparation AE-II exhibit two components, i.e., a component having a molecular weight of about 39,000 (AE-IIa) and another component having a molecular weight of about 34,000 (AE-IIb). These two components also exhibit a similar enzyme activity as the above-mentioned enzyme product AE-I.

Assay of enzyme activity

C-terminal α-amidating enzyme of the present invention is assayed using synthetic peptide [$^{125}$I]-Ac-Tyr-Phe-Gly as a substitute according to the following procedure. [$^{125}$I]-Ac-Tyr-Phe-Gly (1 pmole, 70,000–150,000 cpm) was incubated with an enzyme preparation, in a final volume of 250 μl containing 0.2M Tris-HCl buffer (pH 7.0), 2 μM $CuSO_4$, 0.25 mM ascorbic acid, 25 μg catalase (Boehringer), 0.1% Lubrol (PX type, Nakarai Chemicals). The reaction mixture was kept at 37° C. for 1 to 4 hours. Then 0.75 ml of 1M Tris-HCl buffer (pH 7.0) and 2 ml of the organic phase of an ethyl acetate/water mixture was added. Two phases were mixed vigorously on a Vortex mixer. After centrifugation at 3000 rpm for 3 min, the organic phase thus separated was transferred to another test tube. The radioactivity in organic and aqueous layers was each measured by a gamma scintillation counter. Under the conditions described above, over 98% of radioactivity of the authentic [$^{125}$I]-Ac-Tyr-Phe-Gly was retained in an aqueous phase and over 98% of radioactivity of the authentic [$^{125}$I]-Ac-Tyr-Phe-NH$_2$ was transferred to an organic phase. The yield of conversion was calculated from the ratio of the radioactivity in ethyl acetate phase to the total radioactivity. In this assay, one unit is defined as an amount of enzyme which converts 50% of added substrate [$^{125}$I]-Ac-Try-Phe-Gly to [$^{125}$I]-Ac-Tyr-Phe-NH$_2$.

Where a crude extract from the skin of *Xenopus laevis* is assayed, the above-mentioned ethyl acetate layer is purified by reverse-phase HPLC using a μBondapak C-18 column, (Waters) before measurement of the radioactivity. Elution is carried out with a linear gradient of CH$_3$CN concentration from 10 to 50% in 10 mM ammonium formate (pH 4.0) at a flow rate of 2.0 ml/min. The result is shown in FIG. 1, wherein arrow a shows a point at which authentic peptide [$^{125}$I]-*Ac-Tyr-Phe-Gly elutes, and arrow b shows a point at which authentic peptide* [$^{125}$I]-Ac-Tyr-Phe-NH$_2$ elutes. Since the reaction product elutes at the same point as the authentic [$^{125}$I]-Ac-Tyr-Phe-NH$_2$, it is confirmed that the present enzyme converts the substrate [$^{125}$I]-Ac-Tyr-Phe-gly to [$^{125}$I]-Ac-Tyr-Phe-NH$_2$.

Process for α-amidation of peptide

The present enzyme products can be used to α-amidate a peptide. In this process, a substrate peptide having a glycine residue at its C-terminal is incubated with one of the present enzyme products in an aqueous reaction medium, preferably in an aqueous buffer, such as Tris-HCl, at a pH of about 6 to 7, and at a temperature of about 37° C. for a time sufficient to convert a substantial amount of the starting peptide to a corresponding C-terminal α-amidated peptide.

EXAMPLES

The present invention will now be further illustrated by, but is by no means limited to, the following examples.

EXAMPLE 1

Production of C-terminal α-amidating enzymes

The frog skins (wet weight 48 g) dissected out from *Xenopus laevis* were homogenized with a Polytron homogenizer in 1 liter of 10 mM Tris-HCl buffer (pH 7.0) containing 20 μM CuSo$_4$. After centrifugation at 30,000 g for 30 min, the resulting pellets were reextracted with 600 ml of the same buffer using the Polytron homogenizer and centrifuged. To the combined supernatant solution, solid ammonium sulfate was added to a final concentration of 70% saturation. The resulting precipitate was resuspended in 120 ml of a 2 mM sodium phosphate buffer (pH 8.6) containing 20 μM CuSO$_4$ and dialyzed against the same buffer.

Figure 2:
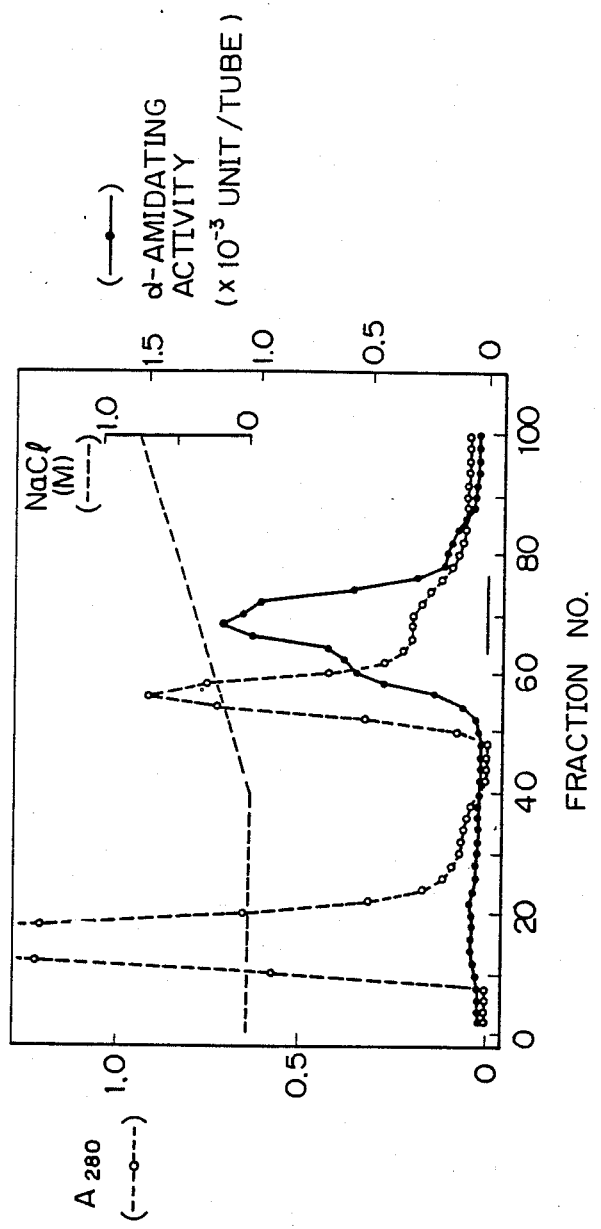
FIG. 2 represents an elution profile of the α-amidating enzymes in Affi-Gel Blue chromatography.

The dialyzate was applied to a column of DEAE-cellulose (DE-52) (4.0×32 cm), and equilibrated with the same buffer. The column was washed with a 2 mM sodium phosphate buffer (pH 8.6) containing 20 μM CuSO$_4$, and then eluted with a 21 linear gradient from 2 mM to 250 mM sodium phosphate buffer (pH 8.6). The enzyme active fractions eluted at the phosphate concentration of 0.04–0.12M were pooled, concentrated with ammonium sulfate precipitation at 80% saturation, and dialyzed against a 5 mM Tris-HCl buffer (pH 7.0) containing 2 μM CuSO$_4$. The dialyzate was applied to a column (4.0×32 cm) of Affi-Gel Blue (Bio Rad), and equilibrated with the same buffer. The column was washed with a 5 mM Tris-HCl buffer (ph 7.0) containing 2 μM CuSO$_4$ and then eluted with a linear gradient from 0 to 1.0M NaCl in the same buffer. Fractions of 20 ml were collected at a flow rate of 40 ml/h (FIG. 2). The enzyme activity was assayed as described above. The major active fractions (Fr: 63–77) were pooled and concentrated by ultrafiltration with a YM-10 membrane (Amicon).

Figure 3:
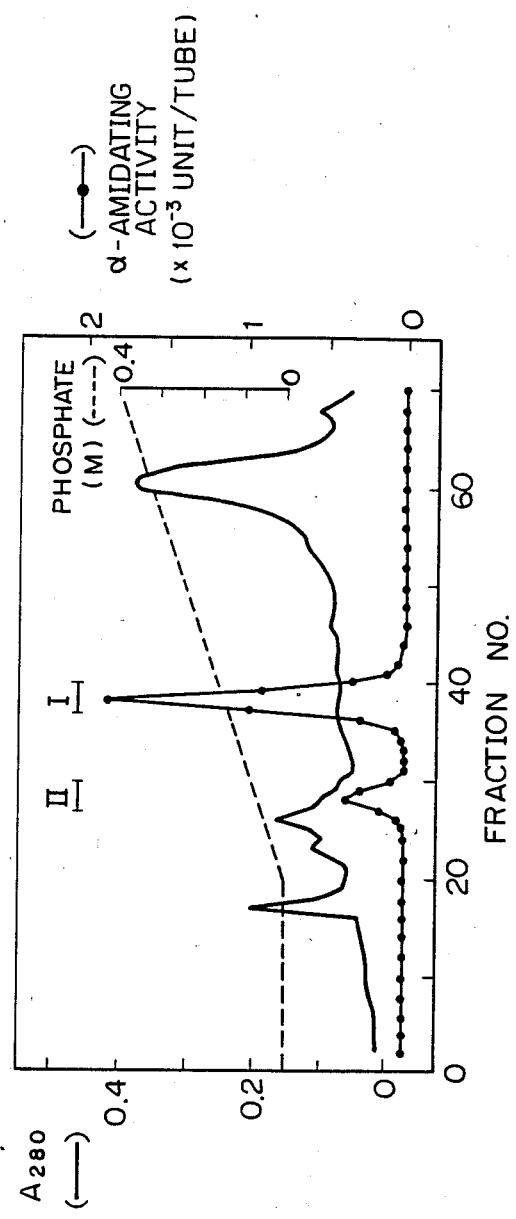
FIG. 3 represents an elution profile of the α-amidating enzymes in column chromatography using hydroxylapatite wherein an AE-I fraction and AE-II fraction are fractionated.
Figure 4:
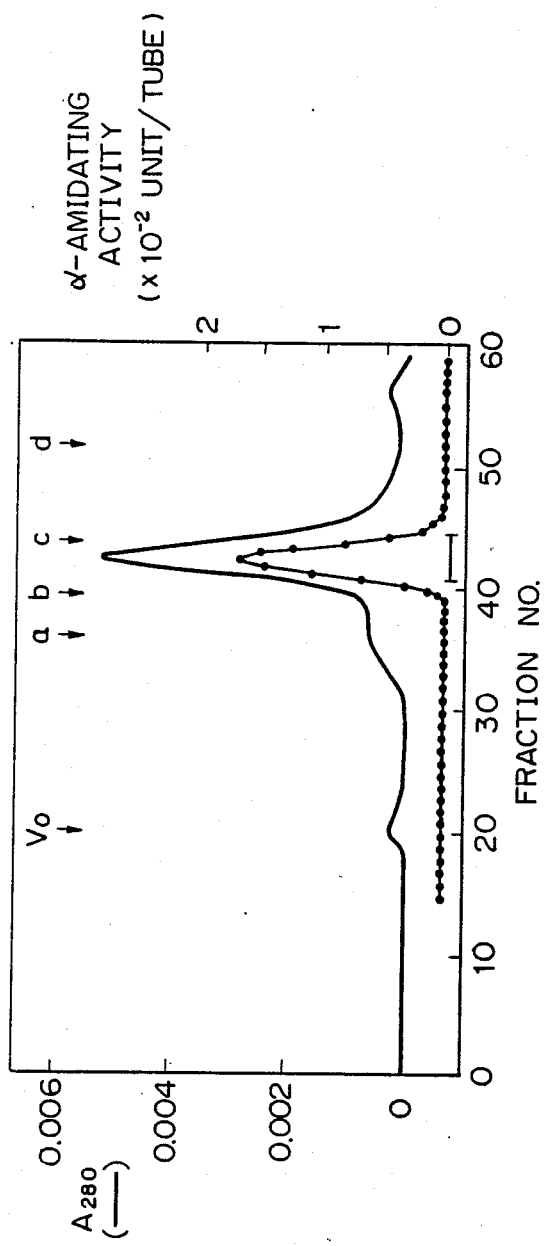
FIG. 4 represents an elution profile of the α-amidating enzyme AE-I in column chromatography using Superose 12 gel.

The concentrate was applied to a column (3.0×140 cm) of Sephacryl S-300, and equilibrated with 50 mM Tris-HCl (pH 7.0)–0.1M NaCl-2 μM CuSO$_4$. The enzyme active fractions eluted in 520–650 ml were pooled, concentrated with a YM-10 membrane and applied to a hydroxylapatite column (1.5×21 cm), equilibrated with 10 mM potassium phosphate buffer (pH 6.8) containing 10 μM CaCl$_2$ and 0.1% Lubrol. The column was washed with the same buffer and the eluted with a linear gradient from the starting buffer to a 0.4M potassium phosphate buffer (pH 6.8) containing 10 μM CaCl$_2$ and 0.1% Lubrol. Fractions of 7 ml were collected at a flow rate of 12 ml/h. Two enzyme activities were observed in Fr. 37–39 (designated as AE-I) and Fr. 27–29 (AE-II). The elution profile is shown in FIG. 3. The major active fractions (AE-I) were pooled, diluted with 2 volumes of distilled water, and further purified by a high-performance hydroxylapatite column (HPHT, Bio Rad) using a linear gradient elution from 0.01 to 0.35M sodium phosphate buffer (pH 6.8) containing 10 μM CaCl$_2$ and 0.1% Lubrol. The enzyme active fractions eluted in the phosphate concentrations of 0.11–0.14M were pooled and subjected to gel-filtration on a column of Superose 12 (prep grade, 1.6×50 cm, Pharmacia), and equilibrated with a 10 mM Tris-HCl buffer (pH 7.0) containing 0.1M NaCl and 0.1% Lubrol. Fractions of 0.75 ml were collected at a flow rate of 1.5 ml/min. The elution profile is shown in FIG. 4. The active fraction (marked with a bar) was collected and the purified enzyme (AE-I) obtained. Starting with 48 g of frog skin, the procedures yielded 27 μg of the purified enzyme with a 2% recovery (Table 1).

On the other hand, the minor active fraction (AE-II) obtained from hydroxylapatite chromatography (FIG. 3) was further purified by the sequential chromatography on an HPHT column and a Superose 12 column in a manner similar as above.

Figure 5:
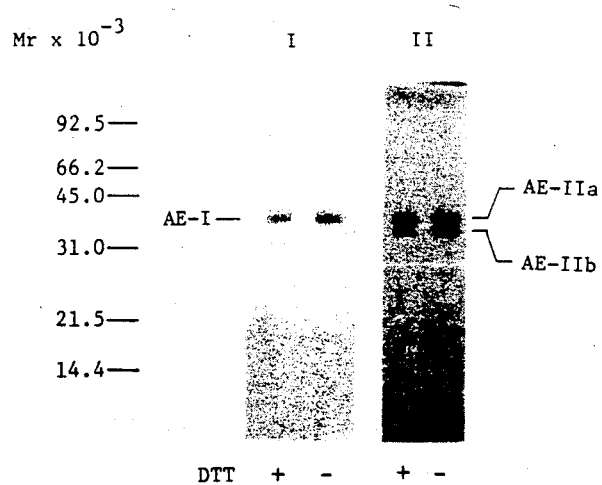
FIG. 5 shows the result of SDS-polyacrylamide gel electrophoresis for the present α-amidating enzyme products AE-I and AE-II, in the presence (+) and absence (−) of dithiothreitol.

The enzyme (AE-I) thus purified was verified to be homogeneous on SDS-polyacrylamide gel electrophoresis using a discontinuous buffer system and silver stain, both in the absence and in the presence of 12.5 mM dithiothreitol. The result is shown in FIG. 5A. As seen from the Figure, both under the presence and absence of DTT, the enzyme preparation AE-I provided only one band corresponding to a molecular weight of about 39,000. Thus, it was concluded that the enzyme consists of a single polypeptide chain with an apparent molecular weight of 39,000. The purity of the enzyme was also confirmed by reverse-phase HPLC. On the other hand, the above-mentioned Superose-purified fraction AE-II was tested according to the same procedure as described for the fraction AE-I. As a result, as shown in FIG. 5B, SDS-gel analysis showed that the AE-II fraction comprises a component (AE-IIa) having a molecular weight of about 39,000 and a component (AE-IIb) having a molecular weight of about 34,000.

Figure 6:
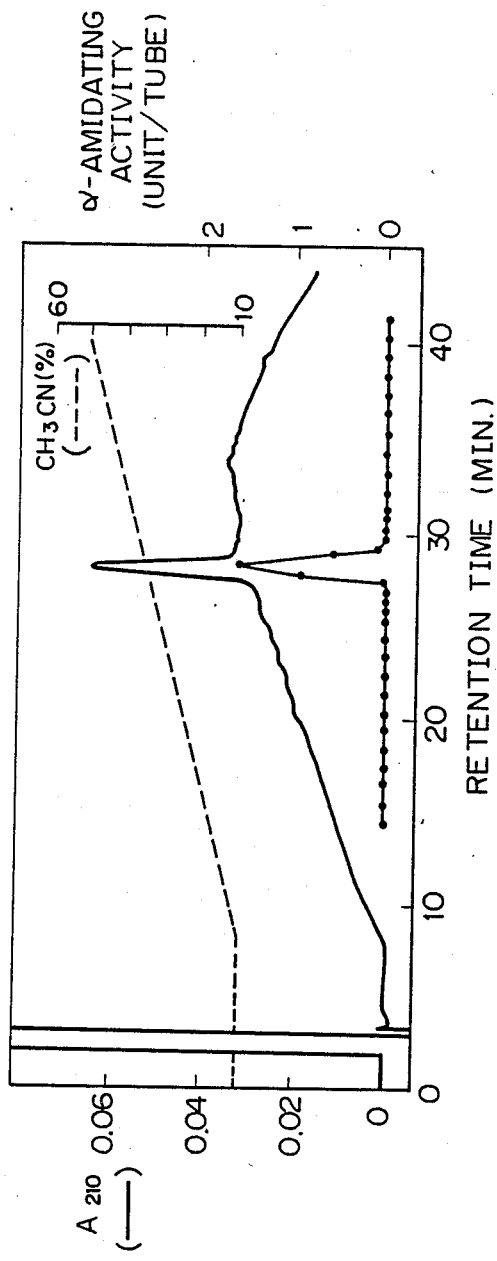
FIG. 6 represents an elution profile of the present α-amidating enzyme AE-I in revers-phase HPLC using a Hipore RP-304 column.

Moreover, the purity of the enzyme product AE-I was analyzed by reverse phase HPLC using Hipore RP-304 (BioRad). That is, 2 μg of the enzyme product AE-I was applied to Hipore RP-304 column, and the elution was carried out by a linear gradient of 10 to 60% $CH_3CN$ in 0.1% trifluoroacetic acid at a flow rate of 1.5 ml/min. As shown in FIG. 6, an enzyme fraction showing a single peak was obtained. By applying the same procedure to the fraction AE-II, the fraction AE-II was purified, and the purified fraction AE-II was separated into its components AE-IIa and AE-IIb by reverse HPLC.

Table 1 shows the steps of the purification of the C-terminal α-amidating enzyme AE-I.

TABLE 1

| | Purification of AE-I from skin of *Xenopus laevis* | | | | |
|---|---|---|---|---|---|
| Step | Total Protein (mg) | Total Activity (Unit) | Specific Activity (Unit/mg) | Yield (%) | Times of Purification |
| 1. Crude Extract | 11376 | 46368 | 4.08 | (100.0) | (1.0) |
| 2. $(NH_4)_2SO_4$ Salting Out | 1681.1 | 40403 | 24.03 | 87.1 | 5.9 |
| 3. DE-52 | 729.0 | 24407 | 33.48 | 52.6 | 8.2 |
| 4. Affi-Gel Blue | 56.30 | 13037 | 231.48 | 28.1 | 56.7 |
| 5. Sephacryl S-300 | 45.20 | 11584 | 256.28 | 25.0 | 62.8 |
| 6. Hydroxylapatite | 1.263 | 3784.2 | 2996.2 | 8.2 | 734.4 |
| 7. HPHT | 0.115 | 1509.0 | 13122 | 3.3 | 3216.1 |
| 8. Superose 12 | 0.027 | 921.4 | 34126 | 2.0 | 8364.2 |

EXAMPLE 2

Partial determination of amino acid sequence

The amino acid sequence at N-terminal of the above-prepared three enzyme fractions AE-I, AE-IIa, and AE-IIb was determined by a conventional stepwise Edman degradation using a gas-phase automated sequencer (Applied Biosystems 470A). As a result, it was found the all three fractions AE-I, AE-IIa, and AE-IIb had a common N-terminal amino acid sequence Ser-Leu-Ser-. Consequently, it appears that the three components of the enzymes of the present invention are related each other.

EXAMPLE 3

Confirmation of amidation by the present enzyme

Figure 7:
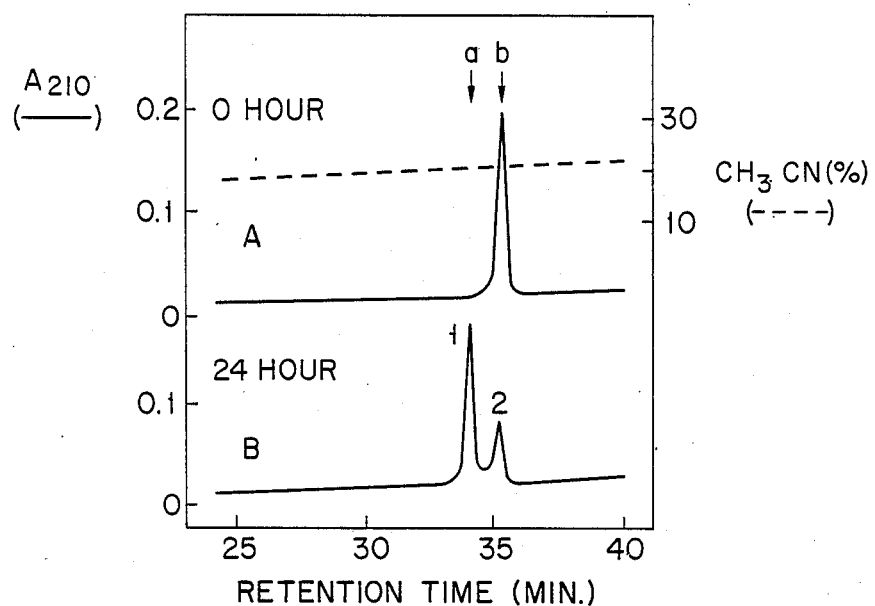
FIG. 7 represents elution profiles in column chromatography using TSK ODS-120A, wherein A is an elution pattern of a substrate Tyr-Gly-Gly-Phe-Met-Arg-Arg-Val-Gly, and B is an elution pattern of a reaction product obtained by treating the substrate with the present α-amidating enzyme product AE-I for 24 hours. In A, arrows a and b show elution points of authentic adrenorphin and the substrate Tyr-Gly-Gly-Phe-Met-Arg-Arg-Val-Gly. The site of peak 1 in B matches the site of the arrow a in A, and the site of peak 2 in B matches the site of the arrow b in A; and, FIG. 8 is a graph showing a rate of conversion of different substrates into corresponding C-terminal α-amidated products by the present α-amidating enzyme product AE-I.

The 0.1 μg of the enzyme preparation AE-I prepared in Example 1 was incubated with 4 nmoles of Tyr-Gly-Gly-Phe-Met-Arg-Arg-Val-Gly as a substrate in 250 μl of a 0.2M Tris-HCl buffer (pH 7.0) containing 2 μM $CuSO_4$, 0.25 mM ascorbic acid, 25 μg catalase, and 0.1% Lubrol, at 37° C. for 24 hours. After the reaction was terminated by the addition of 250 μl of 1% trifluoroacetic acid, the reaction mixture was applied to a TSK ODS-120A column (0.4×25 cm; Toyosoda), and elution was carried out using a linear gradient of 12 to 60% $CH_3CN$ in 0.1% trifluoroacetic acid at a flow rate of 1.5 ml/min. The elute was analyzed for absorbance at 210 nm. The result is shown in FIG. 7. FIG. 7A represents an elution pattern for a sample of the reaction mixture taken at 0 time, i.e., before the reaction, and FIG. 7B represents an elution pattern for a sample of the reaction mixture taken 24 hours after the reaction has started. FIG. 7B shows that about 75% to 80% of the substrate Tyr-Gly-Gly-Phe-Met-Arg-Arg-Val-Gly corresponding to peak 2 was converted to a product corresponding to peak 1. In FIG. 7, arrows b and a represent positions at which the peaks of authentic substrate and authentic adrenorphin Tyr-Gly-Gly-Phe-Met-Arg-Arg-Val-$NH_2$ respectively appear under the same condition. Adrenorphin corresponds to a peptide wherein C-terminal glycine has been converted to α-amide. Since the positions 1 and 2 match the positions a and b respectively, it is reasonable to assume that the reaction product corresponding to peak 1 is adrenorphin. This means that the enzyme of the present invention amidated the substrate at its C-terminal. To confirm this conclusion, the fraction 1 in FIG. 7 was hydrolyzed in 6M HCl at 110° C. for 24 hours, and the amino acid composition of the hydrolyzate was analyzed using an amino acid analyzer. Moreover, the presence of the C-terminal amide group in the fraction 1 was analyzed by thermolysin digestion followed by thin layer chromatography. All of the results confirmed that the reaction product is adrenorphin.

EXAMPLE 4

Specificity to different substrates

Figure 8:
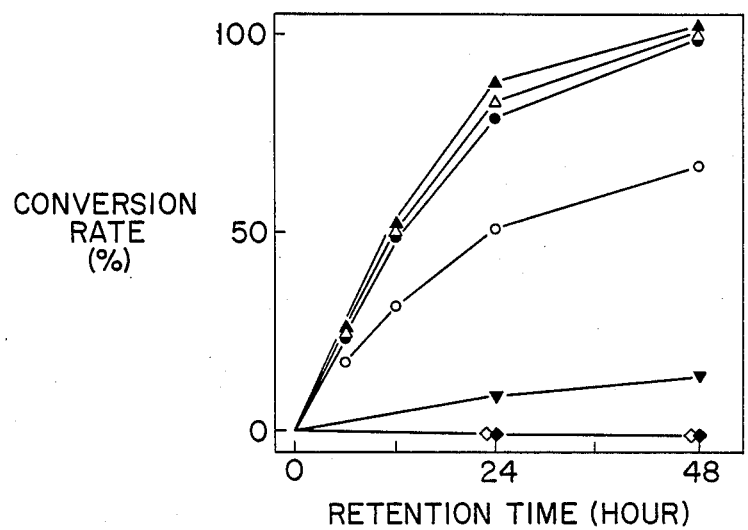

The same procedure as described in Example 3 was repeated except that, in place of Tyr-Gly-Gly-Phe-Met-Arg-Arg-Val-Gly(FIG. 8A), following substrates were used:

Tyr-Phe-Gly,
Ac-Tyr-Phe-Gly,
D-Tyr-Val-Gly,
D-Tyr-Gly-Gly,
Tyr-Gly-Gly-Phe-Met-Arg-Arg-Val, and BAM-12 P (Tyr-Gly-Gly-Phe-Met-Arg-Arg-Val-Gly-Arg-Pro-Glu, The result is shown in FIG. 8. As seen from FIG. 8, four tripeptide substrates all containing the structure of C-terminal Gly residue were converted to the corresponding des-Gly peptide α-amides, although there were some differences in rates (Tyr-Phe-Gly(FIG. 8  )>Ac-Tyr-Phe-Gly(FIG. 8  )>D-Tyr-Val-Gly(FIG. 8  )>D-Tyr-Gly-Gly (FIG. 8  )). On the other hand, desamido-adrenorphin Tyr-Gly-Gly-Phe-Met-Arg-Arg-Val) (FIG. 8  ) and its C-terminally extended peptide, BAM-12P (Tyr-Gly-Gly-Phe-Met-Arg-Arg-Val-Gly-Arg-Pro-Glu) (FIG. 8  ), were not affected by the enzyme, indicating that the enzyme requires C-terminal glycine for α-amidation. Under the standard conditions described above, the kinetic constants of the enzyme AE-I for Ac-Tyr-Phe-Gly were determined from Lineweaver-Burk plots as a Km of 0.35 μM and a Vmax of 1.9 nmol/μg/h.

The present purification of α-amidating enzyme from *Xenopus laevis* skin will serve to give an understanding of the mechanism of α-amide formation in these cells. Furthermore, the purified enzyme has a promising usefulness for the production of C-terminally α-amidated peptides from the peptides with a free α-carboxyl group, especially when synthesized by recombinant DNA techniques.

We claim:

1. A substantially purified C-terminal α-amidating enzyme product from skins of *Xenopus laevis* characterized by the following properties:
   (1) converting a peptide having a glycine residue at its C-terminal to a C-terminal amidated peptide lacking said glycine residue;
   (2) having a molecular weight of about 39,000 as determined by SDS-polyacrylamide gel electrophoresis; and
   (3) having an N-terminal amino acid sequence represented by Ser-Leu-Ser-.

2. An enzyme product according to claim 1, which is AE-I obtained by separating it from an AE-II fraction by hydroxylapatite column chromatography.

3. An enzyme product according to claim 1, which is AE-IIa obtained by separating it from AE-IIb by reverse-phase HPLC, wherein said AE-IIa and AE-IIb are subfractions of AE-II.

4. A substantially purified C-terminal α-amidating enzyme product from skins of *Xenopus laevis* characterized by the following properties:
   (1) converting a peptide having a glycine residue at its C-terminal to a C-terminal amidated peptide lacking said glycine residue:
   (2) having a molecular weight of about 34,000 as determined by SDS gel electrophoresis; and
   (3) having an N-terminal amino acid sequence represented by Ser-Leu-Ser-.

5. A substantially purified C-terminal α-amidating enzyme preparation from skins of *Xenopus laevis* comprising two enzyme components characterized by the following properties;
   (1) converting a peptide having a glycine residue at its C-terminal to a C-terminal amidated peptide lacking said glycine residue;
   (2) one component having a molecular weight of about 39,000 and another component having a molecular weight of about 34,000, both as determined by SDS-polyacrylamide gel electrophoresis; and
   (3) for both components, having an N-terminal amino acid sequence represented by Ser-Leu-Ser.

6. A process for production of a substantially purified C-terminal α-amidating enzyme preparation from skins of *Xenopus laevis*, comprising the following steps:
   (a) obtaining skins from *Xenopus laevis*,
   (b) homogenizing said skins in a buffer,
   (c) extracting a crude enzyme preparation,
   (d) fractionating the crude enzyme preparation into an enzyme fraction AE-I and an enzyme fraction AE-II by chromatography; and
   (e) purifying the fraction AE-I or AE-II to obtain the enzyme preparation AE-I having a molecular weight of about 39,000 or AE-II showing molecular weights of about 39,000 and 34,000, as determined by SDS-polyacrylamide gel electrophoresis.

7. A process according to claim 6 wherein the fractionation in the step (d) is carried out by hydroxylapatite column chromatography.

8. A process according to claim 6 further including the step of fractionating the enzyme fraction AE-II into an enzyme fraction AE-IIa and an enzyme fraction AE-IIb and purifying the fraction AE-IIa or AE-IIb to obtain an enzyme preparation AE-IIa having a molecular weight of about 39,000 or AE-IIb having a molecular weight of about 34,000.

9. A substantially purified C-terminal alpha-amidating enzyme preparation prepared by the process comprising the following steps:
   (a) obtaining skins from *Xenopus laevis*,
   (b) homogenizing said skins in a buffer,
   (c) extracting a crude enzyme preparation,
   (d) fractionating the crude enzyme preparation into an enzyme fraction AE-I and an enzyme fraction AE-II by chromatography; and
   (e) purifying the fraction AE-I or AE-II to obtain the enzyme preparation AE-I having a molecular weight of about 39,000 or AB-II showing molecular weight of about 39,000 and 34,000, as determined by SDS-polyacrylamide gel electrophoresis.

10. A process for C-terminal amidation of a peptide, comprising incubating a starting peptide having a glycine residue at its C-terminal with a C-terminal α-amidating enzyme preparation selected from the enzyme preparations defined in claims 1, 2, 3 or 9 in an aqueous reaction medium to form a target C-terminal α-amidated peptide.

11. A process according to claim 10, wherein the starting peptide is a peptide produced by a recombinant DNA technique and the target peptide is a biologically active peptide.

12. A process according to claim 8 wherein the fractionation is carried out by reverse-phase HPLC.

* * * * *